(12) United States Patent
Kang et al.

(10) Patent No.: US 7,918,989 B2
(45) Date of Patent: Apr. 5, 2011

(54) GAS SENSOR AND METHOD THEREOF

(75) Inventors: Dong-hun Kang, Yongin-si (KR); Wan-jun Park, Seoul (KR); Chan-jin Park, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 1216 days.

(21) Appl. No.: 11/543,932

(22) Filed: Oct. 6, 2006

(65) Prior Publication Data

US 2007/0158209 A1 Jul. 12, 2007

(30) Foreign Application Priority Data

Jan. 5, 2006 (KR) .................. 10-2006-0001389

(51) Int. Cl.
*G01N 27/26* (2006.01)
(52) U.S. Cl. .................. 205/782; 205/780.5; 205/785.5; 204/400; 204/431; 977/920
(58) Field of Classification Search .......... 204/400–402, 204/406–407, 431–433; 205/780.5–781, 205/782–783, 785.5
See application file for complete search history.

(56) References Cited

U.S. PATENT DOCUMENTS

| | | | | |
|---|---|---|---|---|
| 4,495,793 | A * | 1/1985 | Hager | 73/31.05 |
| 6,894,359 | B2 * | 5/2005 | Bradley et al. | 257/414 |
| 6,905,655 | B2 * | 6/2005 | Gabriel et al. | 422/82.01 |
| 2002/0031602 | A1 * | 3/2002 | Zhang | 427/58 |
| 2003/0011312 | A1 * | 1/2003 | Kamimura et al. | 315/149 |
| 2003/0182986 | A1 * | 10/2003 | Hiramoto et al. | 73/23.2 |
| 2004/0147037 | A1 | 7/2004 | Dai et al. | |
| 2005/0244811 | A1 * | 11/2005 | Soundarrajan et al. | 435/4 |
| 2006/0000259 | A1 * | 1/2006 | Rothschild et al. | 73/31.06 |
| 2007/0108484 | A1 * | 5/2007 | Nagamune et al. | 257/290 |

FOREIGN PATENT DOCUMENTS

WO WO2005/008787 * 1/2005

OTHER PUBLICATIONS

Korean Office Action dated Dec. 19, 2006.
Jing Kong et al., "Nanotube Molecular Wires as Chemical Sensors", Science vol. 287, Jan. 28, 2000.

* cited by examiner

*Primary Examiner* — Nam X Nguyen
*Assistant Examiner* — Bach T Dinh
(74) *Attorney, Agent, or Firm* — Harness, Dickey & Pierce, P.L.C.

(57) ABSTRACT

A gas sensor and method thereof are provided. The example gas sensor may include first and second electrodes formed on a substrate, a carbon nanotube connecting the first and second electrodes on the substrate, a light source disposed above the carbon nanotube and an ampere meter measuring current flowing between the first and second electrodes. The example method may be directed to identifying a gas, and may include measuring a first current responsive to a first applied voltage during a first mode of operation, comparing the first measured current with a plurality of first index current values to obtain a first comparison result, each of the plurality of first index current values associated with one of a plurality of gases, measuring a second current responsive to a second applied voltage during a second mode of operation, comparing the second measured current with a plurality of second index current values to obtain a second comparison result, each of the plurality of second index current values associated with one of the plurality of gases and determining gas characteristic information based on the first and second comparison results.

9 Claims, 4 Drawing Sheets

US 7,918,989 B2

GAS SENSOR AND METHOD THEREOF

PRIORITY STATEMENT

This application claims the benefit of Korean Patent Application No. 10-2006-0001389, filed on Jan. 5, 2006, in the Korean Intellectual Property Office, the disclosure of which is incorporated herein in its entirety by reference.

BACKGROUND OF THE INVENTION

1. Field of the Invention

Example embodiments of the present invention relate generally to gas sensor and method thereof, and more particularly to a gas sensor and method of identifying a gas.

2. Description of the Related Art

Carbon nanotubes may have relatively high electric conductivity and thermal stability, and may be formed with a longitudinal shape having a given diameter (e.g., from several to tens of nanometers and to a few micrometers). Carbon nanotubes may be deployed within microstructural nano electro-mechanical system (NEMS) devices. Also, carbon nanotubes may be applied to electric field emission devices, optical switches used in the optical communications field, and bio devices.

A conventional gas sensor may be configured to include carbon nanotubes. The conventional gas sensor may detect whether or not a given gas may be present during an application of a gate voltage. Generally, each conventional gas sensor may be configured to detect a single type of gas. Thus, in order to detect multiples types of gases, more than one gas sensor may be deployed. Also, a pressure sensor may also be included, in addition to the multiple gas sensors, to measure a concentration or density of the gases.

SUMMARY OF THE INVENTION

An example embodiment of the present invention is directed to a gas sensor, including first and second electrodes formed on a substrate, a carbon nanotube connecting the first and second electrodes on the substrate, a light source disposed above the carbon nanotube and an ampere meter measuring current flowing between the first and second electrodes.

Another example embodiment of the present invention is directed to a method of identifying a gas, including measuring a first current responsive to a first applied voltage during a first mode of operation, comparing the first measured current with a plurality of first index current values to obtain a first comparison result, each of the plurality of first index current values associated with one of a plurality of gases, measuring a second current responsive to a second applied voltage during a second mode of operation, comparing the second measured current with a plurality of second index current values to obtain a second comparison result, each of the plurality of second index current values associated with one of the plurality of gases and determining gas characteristic information based on the first and second comparison results.

Another example embodiment of the present invention is directed to a gas sensor using carbon nanotube which may determine the type and concentration of a gas.

Another example embodiment of the present invention is directed to a method of measuring a type and concentration of a gas using a gas sensor.

BRIEF DESCRIPTION OF THE DRAWINGS

The accompanying drawings are included to provide a further understanding of the invention, and are incorporated in and constitute a part of this specification. The drawings illustrate example embodiments of the present invention and, together with the description, serve to explain principles of the present invention.

DETAILED DESCRIPTION OF EXAMPLE EMBODIMENTS OF THE PRESENT INVENTION

Figure 1:
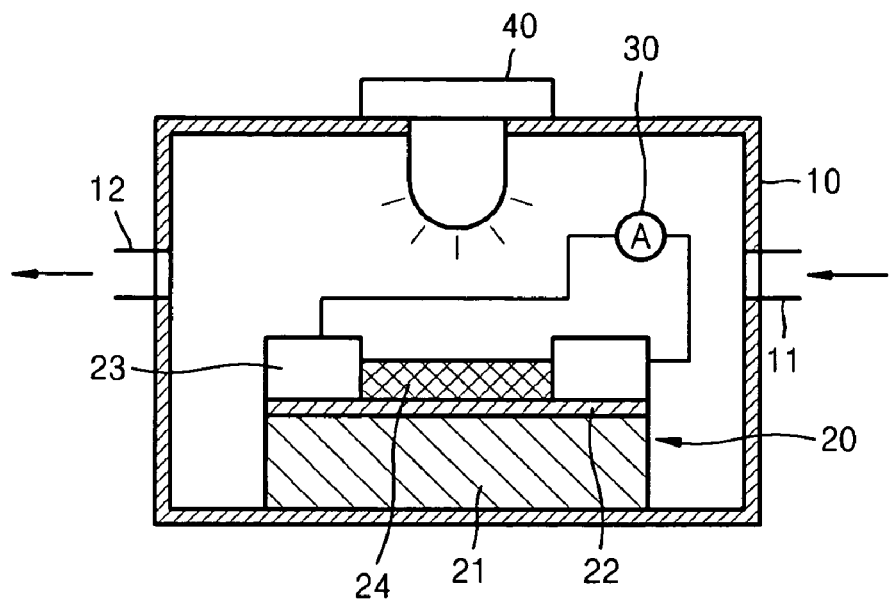
FIG. 1 is a schematic view illustrating a gas sensor including carbon nanotubes according to an example embodiment of the present invention.

Detailed illustrative example embodiments of the present invention are disclosed herein. However, specific structural and functional details disclosed herein are merely representative for purposes of describing example embodiments of the present invention. Example embodiments of the present invention may, however, be embodied in many alternate forms and should not be construed as limited to the embodiments set forth herein.

Accordingly, while example embodiments of the invention are susceptible to various modifications and alternative forms, specific embodiments thereof are shown by way of example in the drawings and will herein be described in detail. It should be understood, however, that there is no intent to limit example embodiments of the invention to the particular forms disclosed, but conversely, example embodiments of the invention are to cover all modifications, equivalents, and alternatives falling within the spirit and scope of the invention. Like numbers may refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. Conversely, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof. Likewise, layered relational terms such as "on" are not intended to be construed as "directly" on, but rather may also refer to example embodiments wherein intervening layers may be present. Further, relative directional terms such as "above", "below", "right", "left", etc. are used to provide a reader with an understanding of example embodiments of the present invention in view of the particular orientations illustrated in the drawings, and as such, it will be appreciated that such relative terms may be adjusted in other orientations of the same.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic view illustrating a gas sensor 20 including carbon nanotubes 24 according to an example embodiment of the present invention.

In the example embodiment of FIG. 1, the gas sensor 20 may be positioned (e.g., in a fixed position) within a vacuum chamber 10. A silicon substrate 21 may be positioned (e.g., in a fixed position) at the bottom of the vacuum chamber 10. An insulation layer 22 may include, for example, silicon oxide, and may be formed on the silicon substrate 21. Two electrodes 23 (e.g., separated by a given distance) may be formed on the insulation layer 22. The carbon nanotubes 24 may connect the respective electrodes 23. In an example, the carbon nanotubes 24 may be network carbon nanotubes, which may grow irregularly from metal catalysts (not illustrated) formed on the insulation layer 22 and may electrically connect the respective electrodes 23. In another example, the gas sensor 20 may be "detachably" (e.g., in a non-fixed manner) mounted on the bottom of the vacuum chamber 10.

In the example embodiment of FIG. 1, in the vacuum chamber 10, a light source 40 (e.g., a light bulb or diode) may be positioned above the carbon nanotubes 24. The light source 40 may excite the carbon nanotubes 24, which may in turn generate and emit electron-hole pairs, thereby changing a level of current flowing through the carbon nanotubes 24. An ampere meter 30 may be connected to the electrodes 23 to measure a level of current flowing through the carbon nanotube 24.

In the example embodiment of FIG. 1, a gas inlet 11 and a gas outlet 12 may be positioned in the vacuum chamber 10. If the vacuum chamber 10 is disposed in a gaseous environment, gas may be injected into the vacuum chamber 10 through the gas inlet 11. The injected gas may flow out of the vacuum chamber 10 through the gas outlet 12. Accordingly, the gas pressure in the vacuum chamber 10 may be maintained at a given concentration or equilibrium. The gas sensor 20 may concurrently (e.g., simultaneously) determine a type and concentration of the gas in the equilibrium state.

Figure 2:
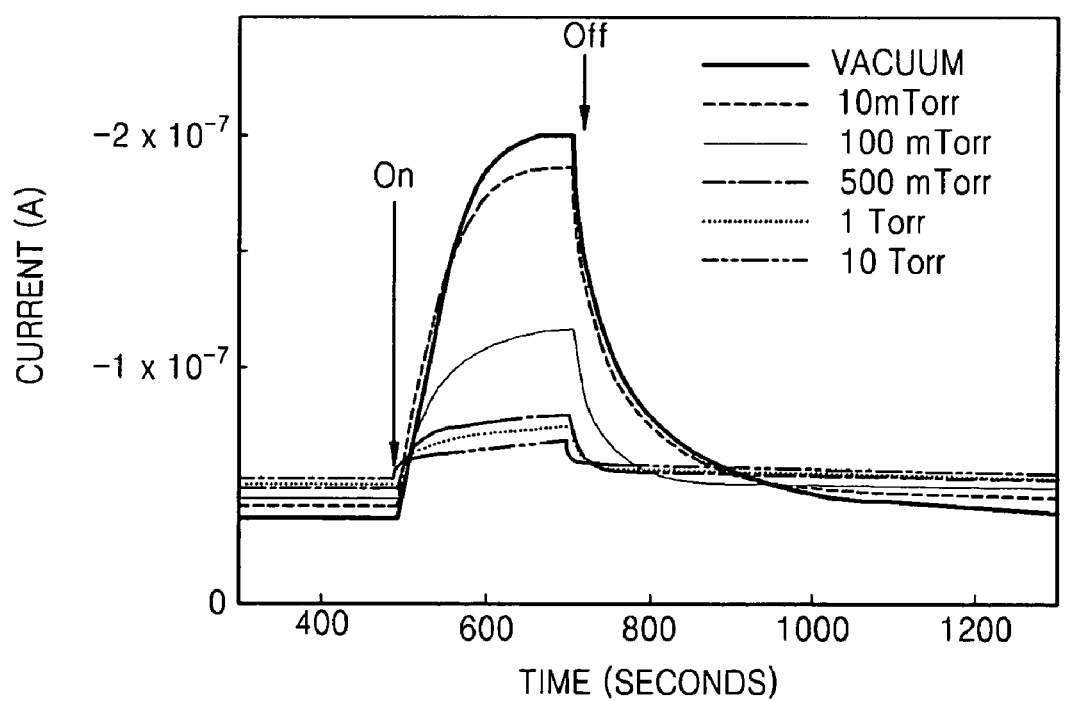
FIG. 2 is a graph illustrating time versus current during a measurement process according to another example embodiment of the present invention.
Figure 3:
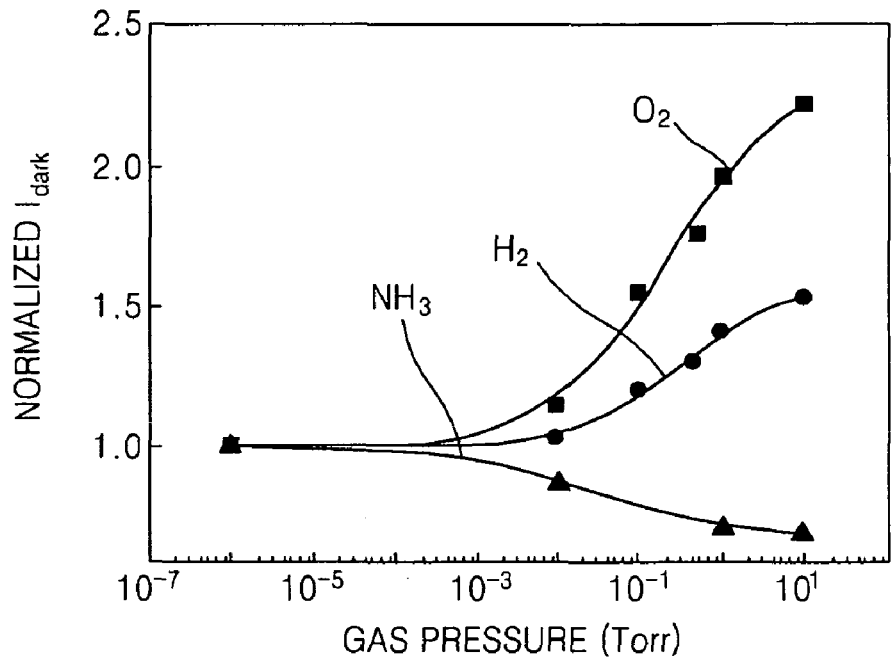
FIG. 3 is a graph illustrating normalized I_dark currents versus gas pressures of hydrogen gas ($H_2$), oxygen gas ($O_2$), and ammonia gas ($NH_3$), respectively, during a measurement process according to another example embodiment of the present invention.
Figure 4:
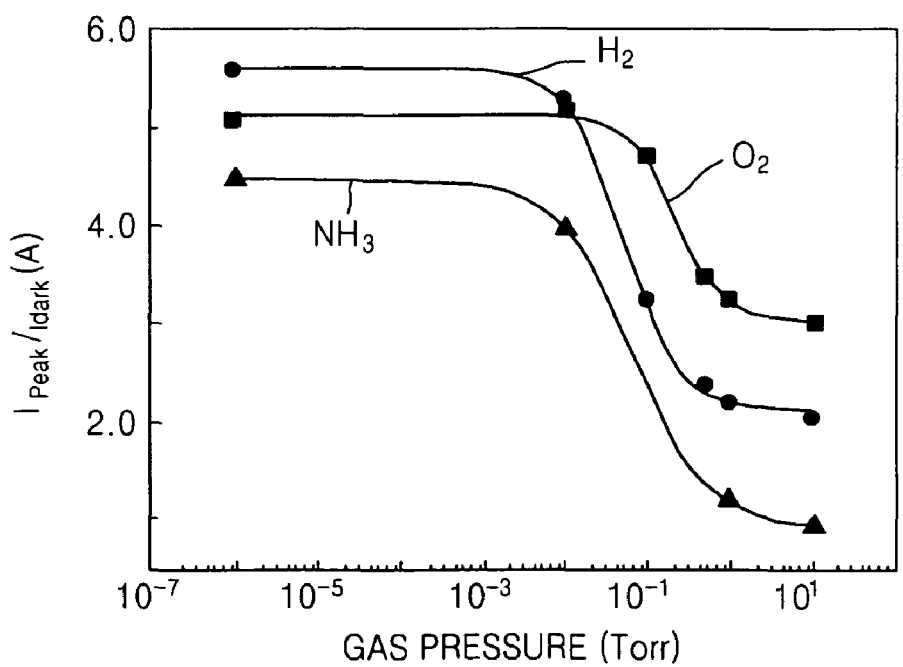
FIG. 4 is a graph illustrating the value of I_peak/I_dark versus gas pressures of hydrogen gas ($H_2$), oxygen gas ($O_2$), and ammonia gas ($NH_3$), respectively, during a measurement process according to another example embodiment of the present invention.

FIGS. 2 through 4 are graphs illustrating data which may be included in a database for measuring the type and concentration of gas injected into the vacuum chamber 10 using the gas sensor 20 of FIG. 1 according to other example embodiments of the present invention.

In particular, FIG. 2 is a graph illustrating time versus current during a measurement process, which will now be described in greater detail. In the example embodiment of FIG. 2, a given voltage (e.g., 5 V) may be applied to the electrodes 23, and hydrogen gas may be injected into the vacuum chamber 10 through the gas inlet 11 to obtain pressures of 0.01, 0.1, 0.5, 1, and 10 Torr. Current flowing through the carbon nanotubes 24 may be measured by the ampere meter 30 corresponding to the different measured pressures of the injected hydrogen gas of the vacuum chamber 10. As will be described later with respect to the example embodiment of FIG. 3, as the concentration or pressure of the hydrogen gas increases, the measured current (I_dark) may increase, and vice versa.

In the example embodiments of FIG. 2, the light source 40 (e.g., a halogen lamp) may be disposed at a distance of 15 cm from the substrate 21 and may radiate 7 mW/mm$^2$ of light onto the substrate 21 for 210 seconds, and thus a current (I_photo) may increase. If the light source 40 is turned off, I_dark may be measured again. In an example, I_photo may increase as the concentration of the hydrogen gas (e.g., the gas pressure) decreases. In the example embodiment of FIG. 2, indicators "On" and "Off" may indicate a turn-on and a turn-off of the light source 40, respectively.

FIG. 3 is a graph illustrating normalized I_dark currents versus gas pressures of hydrogen gas ($H_2$), oxygen gas ($O_2$), and ammonia gas ($NH_3$), respectively, during a measurement process according to another example embodiment of the present invention.

In the example embodiment of FIG. 3, if hydrogen gas and oxygen gas is injected into the vacuum chamber 10, the normalized I_dark may increase as the gas pressure increases. In an alternative example, if ammonia gas is injected into the vacuum chamber 10, normalized I_dark may decrease as the gas pressure increases. Accordingly, it will be appreciated that the value of the normalized I_dark may be used to determine the type and concentration of gases in the vacuum chamber 10.

FIG. 4 is a graph illustrating the value of I_peak/I_dark versus gas pressures of hydrogen gas ($H_2$), oxygen gas ($O_2$), and ammonia gas ($NH_3$), respectively, during a measurement process according to another example embodiment of the present invention. In the example embodiment of FIG. 4, I_peak may denote a peak value of I_photo.

In the example embodiment of FIG. 4, the value of I_peak/I_dark may vary based on a type of the gas included in the vacuum chamber 10 (e.g., hydrogen, oxygen and ammonia), and may further vary based upon a pressure or concentration of the respective gases.

In view of the example embodiments of FIGS. 2 and 4, which illustrate data obtained in a measurement process employing the gas sensor 20 of the example embodiment of FIG. 1, it will be appreciated that one or more of a plurality of gases may be identified based upon a measured current (e.g., via ampere meter 30) and associated pressure reading. Thus, a database of the values of I_dark and I_peak/I_dark for (e.g., for at least the three gases including hydrogen, oxygen and ammonia) may be obtained with the above-described process, at different pressures, according to an example embodiment of the present invention.

Figure 5:
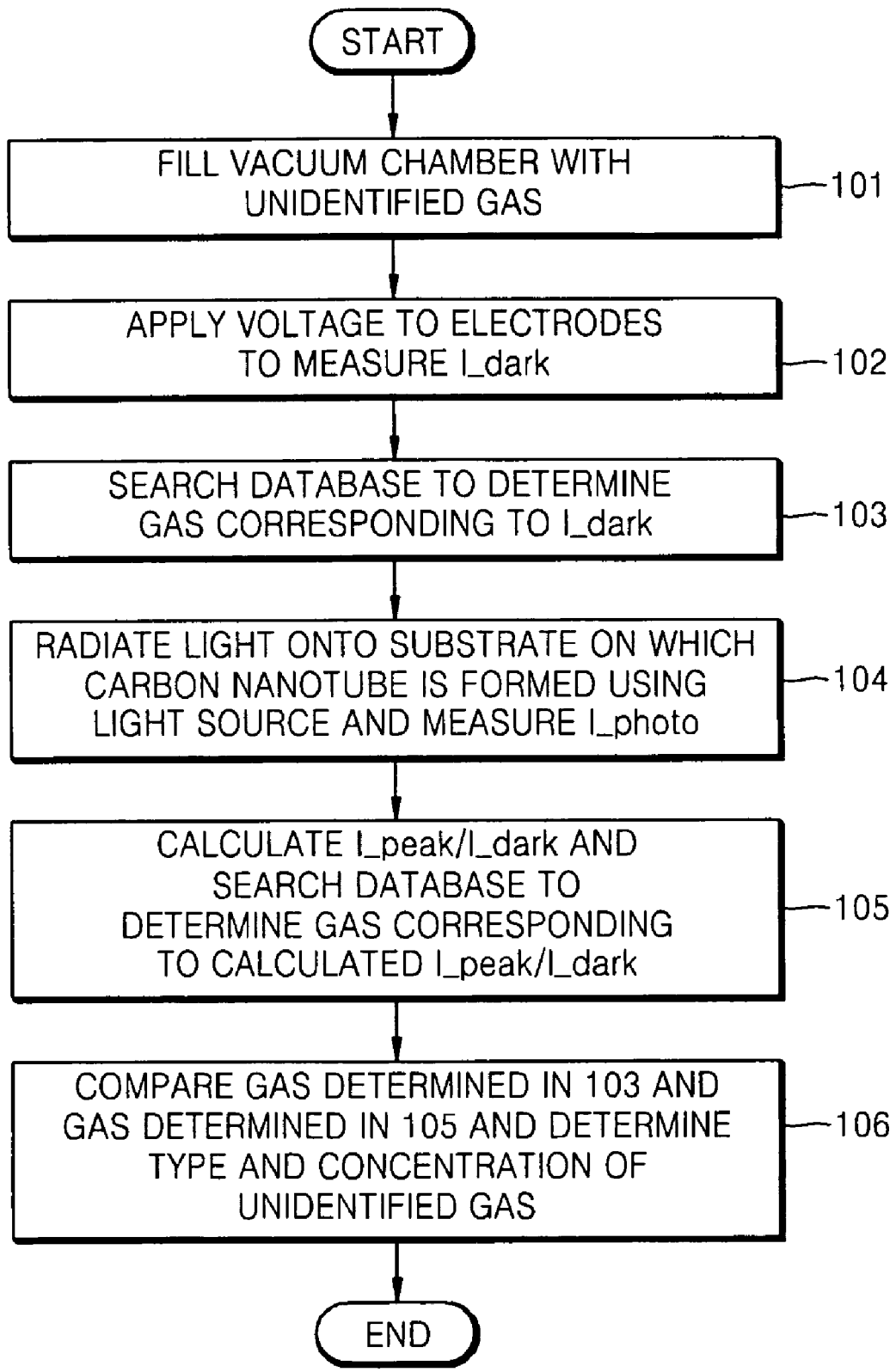
FIG. 5 is a flowchart illustrating a method of measuring the type and concentration of a gas according to another example embodiment of the present invention.

FIG. 5 is a flowchart illustrating a method of measuring the type and concentration of a gas according to another example embodiment of the present invention. FIG. 5 is described below with respect to the example embodiment of FIG. 1.

In the example embodiment of FIG. 5, the gas inlet 11 of the vacuum chamber 10, in which the gas sensor 20 may be mounted, may be opened in a chamber (not illustrated) filled with an unidentified gas so as to inject or fill the vacuum chamber 10 with the unidentified gas (at 101). After the unidentified gas fills the vacuum chamber 10, a given voltage may be applied to the electrodes 23 to measure I_dark (at 102). The measured value of I_dark may be used to search through a database, including gas identifications and associated I_dark values, to identify a gas or gases corresponding to the measured value of I_dark (at 103). For example, the database may be generated in accordance with the measurement and data collection process described above with respect to FIGS. 2 through 4.

Figure 6A:
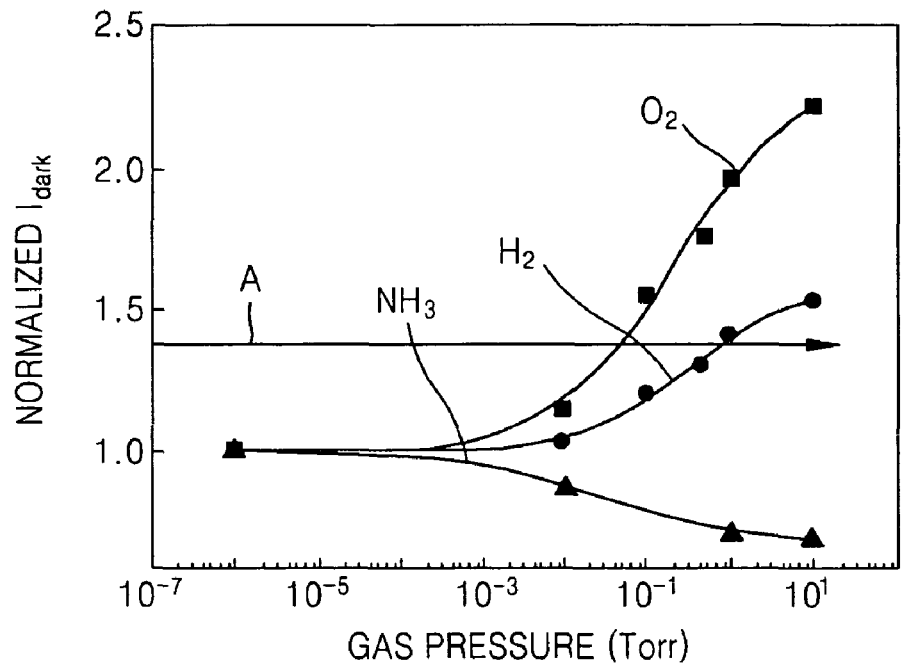
FIG. 6A is a graph illustrating normalized I_dark values for hydrogen gas ($H_2$), oxygen gas ($O_2$), ammonia gas (NH3) according to another example embodiment of the present invention.

FIG. 6A is a graph illustrating normalized I_dark values for hydrogen gas ($H_2$), oxygen gas ($O_2$), ammonia gas ($NH_3$) according to another example embodiment of the present invention. In the example embodiment of FIG. 6A, if the normalized value of I_dark is 1.4, as indicated by a line A, the curves corresponding to hydrogen gas and oxygen gas may be possible candidates for the unidentified gas. For example, if the unidentified gas is hydrogen gas, the gas pressure may be $1 \times 10^0$ Torr. Alternatively, if the unidentified gas is oxygen gas, the gas pressure may be $8 \times 10^{-2}$ Torr.

Returning to the example embodiment of FIG. 5, a voltage may be applied to the light source 40 for a given period of time. The light source 40 may radiate light onto the substrate 21, upon which the carbon nanotubes 24 may be formed, and I_photo may be measured (at 104). The value of I_peak/I_dark may be calculated, and the gas corresponding to the value of I_peak/I_dark may be searched for in the database (at 105).

Figure 6B:
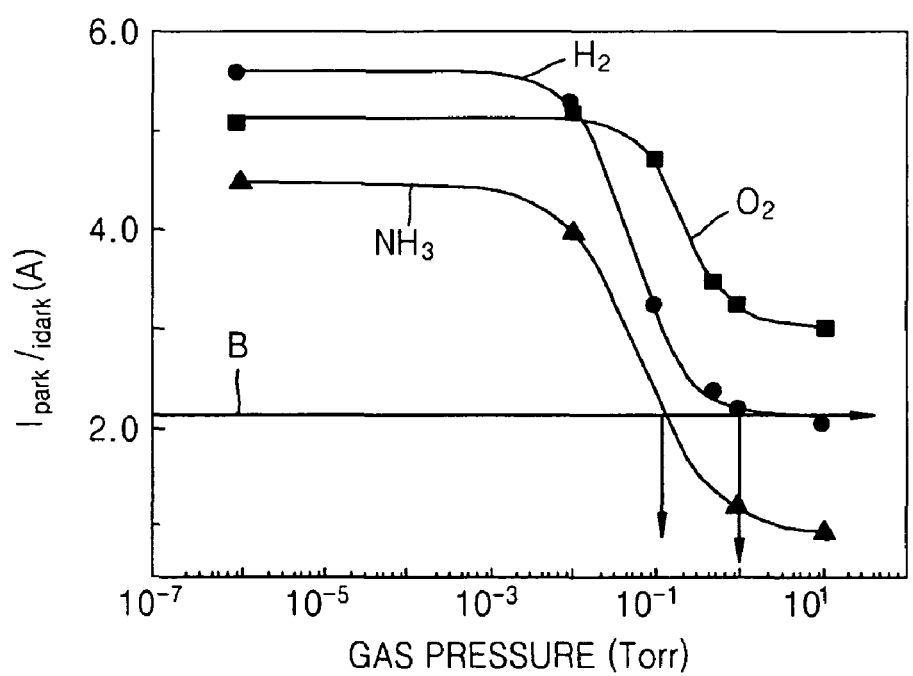
FIG. 6B is a graph illustrating the I_peak/I-dark according to another example embodiment of the present invention.

FIG. 6B is a graph illustrating the I_peak/I-dark according to another example embodiment of the present invention. In the example embodiment of FIG. 6B, if the calculated value of I_peak/I-dark is 2.1, as indicated by a line B, the curves corresponding to hydrogen gas and ammonia gas may be possible candidates for the unidentified gas. For example, if the unidentified gas is hydrogen gas, the gas pressure may be about $1 \times 10^0$ Torr. Alternatively, if the unidentified gas is ammonia gas, the gas pressure may be about $1 \times 10^{-1}$ Torr.

Returning to the example embodiment of FIG. 5, by comparing the type and pressure of the gas (determined in 103) with the type and pressure of the gas determined (determined in 105), the type and concentration of the gas may be determined for the unidentified gas (at 106). Thus, the potential candidates for the unidentified gas from 103 and 105 may be compared, and if only one candidate gas overlaps between the candidate sets from 103 and 105, then the "unidentified" gas may be identified as the overlapping candidate gas, at the associated pressure. For the example values mentioned above, the unidentified gas may be hydrogen gas, and the gas pressure thereof may be equal to 1 Torr. It will be appreciated that the concentration of the hydrogen gas in the vacuum chamber 10 may be calculated based on the gas pressure.

In another example embodiment of the present invention, a single gas sensor may concurrently (e.g., simultaneously) determine a type and concentration of any one of a plurality of gases (e.g., if information associated with the unidentified gas is stored in an associated database).

Example embodiments of the present invention being thus described, it will be obvious that the same may be varied in many ways. For example, while above-described example embodiments of the present invention are directed generally to hydrogen gas, oxygen and ammonia gas, it will be appreciated that other example embodiments of the present invention may be directed to any type of gas. In such example embodiments, data for gases other than oxygen, hydrogen and ammonia may be obtained and added to a database which may thereafter be used to compare against measured values to identify gases in a vacuum chamber.

Further, while specific values are provided in the above example embodiments of the present invention for the purpose of clarity (e.g., 7 mW/mm$^2$ of light radiated by the light source 40, etc.), it is understood that other example embodiments of the present invention may apply any well-known voltage, any well-known light, gas pressure, etc., without falling outside the scope of the present invention.

Such variations are not to be regarded as a departure from the spirit and scope of example embodiments of the present invention, and all such modifications as would be obvious to one skilled in the art are intended to be included within the scope of the following claims.

What is claimed is:

1. A method of measuring a gas, comprising:
   measuring a first current responsive to a first applied voltage during a first mode of operation;
   comparing the first measured current with a plurality of first index current values to obtain a first comparison result, each of the plurality of first index current values associated with one of a plurality of gases;
   measuring a second current responsive to a second applied voltage during a second mode of operation;
   comparing the second measured current with a plurality of second index current values to obtain a second comparison result, each of the plurality of second index current values associated with one of the plurality of gases; and
   determining gas characteristic information based on the first and second comparison results, wherein
   the first and second currents are associated with one or more carbon nanotubes,
   the first applied voltage is applied directly to a carbon nanotube,
   the second applied voltage is applied to a light source,
   the second measured current corresponds to a current generated in a carbon nanotube responsive to light radiated from the light source powered by the second applied voltage,
   the gas characteristic information includes a type of a gas and a concentration of the gas,
   the first mode of operation is a dark mode wherein no radiated light affects the first measured current and the second mode of operation is a light mode where radiated light affects the second measured current, and
   the first voltage and the second voltage are applied simultaneously.

2. The method of claim 1, wherein the first and second comparison results include a set of potential gases which may correspond to the first and second measured currents, respectively.

3. The method of claim 1, further comprising:
   filling a vacuum chamber with an unidentified gas before performing the measuring and comparing steps, the measuring and comparing steps configured to identify a type of the unidentified gas and a concentrated concentration of the unidentified gas.

4. The method of claim 1, measuring the second current includes:
    obtaining a peak value of measured currents as the second measured current in response to the second applied voltage.

5. The method of claim 4, further comprising:
    calculating a value based on the first and second measured currents.

6. The method of claim 5, wherein the determining step includes:
    searching a database for the gas characteristic information based upon the calculated value.

7. The method of claim 1, wherein the first current is generated in response to the first applied voltage having a first magnitude applied across the one or more carbon nanotubes and the second current is generated in response to the second applied voltage and the first applied voltage having the first magnitude applied across the one or more carbon nanotubes.

8. The method of claim 1, wherein the first current and the second current are generated by applying the first voltage across the one or more carbon nanotubes.

9. The method of claim 1, wherein the first index current value is a normalized dark current value and the second index current value corresponds to a ratio of photocurrent to a dark current, the photocurrent being generated in at least one carbon nanotube by applying a voltage across the at least one carbon nanotube and irradiating the at least one carbon nanotube with light.

* * * * *